(12) United States Patent
Gulyas et al.

(10) Patent No.: US 7,439,045 B2
(45) Date of Patent: Oct. 21, 2008

(54) PH CONTROLLED FERMENTATION PROCESS FOR PSEUDOMONIC ACID PRODUCTION

(75) Inventors: Eva Gulyas, Debrecen (HU); Gabor Balogh, Debrecen (HU); Janos Erdei, Debrecen (HU); Peter Seress, Debrecen (HU)

(73) Assignee: TEVA Gyógyszergyár Zártkörúen Müködö Részvénytársaság, Debrecen (HU)

( * ) Notice: Subject to any disclaimer, the term of this patent is extended or adjusted under 35 U.S.C. 154(b) by 0 days.

(21) Appl. No.: 10/177,026

(22) Filed: Jun. 21, 2002

(65) Prior Publication Data

US 2003/0027292 A1 Feb. 6, 2003

Related U.S. Application Data

(60) Provisional application No. 60/299,927, filed on Jun. 21, 2001.

(51) Int. Cl.
C12P 17/16 (2006.01)

(52) U.S. Cl. ............... 435/125; 435/123; 435/117; 435/136; 435/252.3

(58) Field of Classification Search ............. 635/125, 635/253.3, 123
See application file for complete search history.

(56) References Cited

U.S. PATENT DOCUMENTS

| | | | |
|---|---|---|---|
| 3,954,872 A | 5/1976 | Koppe et al. | |
| 3,977,943 A | 8/1976 | Barrow et al. | |
| 4,071,536 A | 1/1978 | Barrow et al. | |
| 4,196,214 A | 4/1980 | Clayton | |
| 4,222,942 A * | 9/1980 | O'Hanlon et al. | 549/414 |
| 4,289,703 A | 9/1981 | Barrow et al. | |
| 4,524,075 A | 6/1985 | Oduro-Yeboah | |
| 4,639,534 A | 1/1987 | Curzons | |
| 4,786,742 A | 11/1988 | Curzons | |
| 4,790,989 A | 12/1988 | Hunter et al. | |
| 4,879,287 A | 11/1989 | Orr et al. | |
| 4,916,155 A | 4/1990 | Baker et al. | |
| 5,191,093 A | 3/1993 | Baker et al. | |
| 5,405,762 A * | 4/1995 | Takahashi et al. | 435/118 |
| 5,436,266 A | 7/1995 | Baker et al. | |
| 5,569,672 A | 10/1996 | Baker et al. | |
| 5,594,026 A | 1/1997 | Greenway et al. | |
| 6,001,870 A | 12/1999 | Henkel | |
| 6,231,875 B1 | 5/2001 | Sun et al. | |
| 6,245,921 B1 | 6/2001 | Barta et al. | |
| 6,489,358 B2 | 12/2002 | Lavon et al. | |
| 6,506,591 B2 | 1/2003 | Szell et al. | |
| 2002/0004063 A1 | 1/2002 | Zhang | |
| 2002/0028227 A1 | 3/2002 | Yu et al. | |
| 2002/0028843 A1 | 3/2002 | Lavon et al. | |
| 2002/0035061 A1 | 3/2002 | Krieger et al. | |
| 2004/0039049 A1 | 2/2004 | Weisman et al. | |

FOREIGN PATENT DOCUMENTS

| | | |
|---|---|---|
| BE | 870855 | 3/1979 |
| DE | 2227739 | 1/1973 |
| EP | 0 005 614 | 11/1979 |
| EP | 0 183 424 | 6/1986 |
| EP | 0 251 434 | 1/1988 |
| EP | 1 174 133 A1 | 1/2002 |
| EP | 1 384 721 A1 | 1/2004 |
| GB | 1395907 | 5/1975 |
| GB | 1577730 | 10/1977 |
| GB | 1577545 | 10/1980 |
| JP | 52-70083 | 6/1977 |
| JP | 52070083 * | 6/1977 |
| WO | 00/46388 | 8/2000 |
| WO | 00/46389 | 8/2000 |

OTHER PUBLICATIONS

Sikyta et al., "Methods in Industrial Microbiology", John Wiley Sons. 1983, pp. 193-199.*
Demain et al., Industrial Microbiology and Biotechnology, American Society of Microbiology. 1986., pp. 333-334.*
A.T. Fuller et al., "Pseudomonic Acid: an Antibiotic Produced by Pseudomonas Fluorescens," Nature, vol. 234, No. 5329, Dec. 17, 1971, pp. 416-417.
Ben Zion Dolitzky et al. "Process for Preparing Nateglinide and Intermediates Thereof" U.S. Appl. No. 60/413,622, filed on Sep. 25, 2002.
Harry G. Brittain (Ed.) (1999) "Polymorphism in Pharmaceutical Solids" Drugs and the Pharmaceutical Sciences vol. 95, pp. 183-226 Marcel Dekker, Inc. New York, New York.
U.S. Appl. No. 10/289,919, filed Nov. 6, 2002 "Processes for Preparing Crystalline and Amorphous Mupirocin Calcium".
U.S. Appl. No. 10/293,675, filed Nov. 12, 2002 "Process for the Preparation of Pseudomonic Acid A Antibiotic by Microbiological Method".
European Pharmacopoeia, 4th Ed. pp. 1602-1604, Strasbourg, (2001).

(Continued)

Primary Examiner—Irene Marx
(74) Attorney, Agent, or Firm—Kenyon & Kenyon LLP

(57) ABSTRACT

An improved fermentation process for preparing pseudomonic acid A (mupirocin) is disclosed. The metabolically controlled fermentation process provides culturing a *Pseudomonas* sp. strain in a submerged medium at a temperature within about 20-30° C. The pH of the fermentation medium is regulated to be at about 5.5-6.0 by feeding the fermentation medium with an assimilable carbon source, a mineral salt, or an acidic/alkali solution. Accordingly, the resulting fermentation broth contains an increased yield of highly purified pseudomonic acid A as the main component. The pseudomonic acid B as an impurity in the fermentation broth is significantly decreased.

28 Claims, No Drawings

OTHER PUBLICATIONS

Clayton et al. "The Structure and Configuartion of Pseudomonic Acid C" Tetrahedron Letters 1980, vol. 21, pp. 881-884.

O'Hanlon et al. "The Chemistry of Pseudomonic Acid. Part 6. Structure and Preparation of Pseudomonic Acid D" Journal Chemical Society, Perkin Trans. I 1983, pp. 2655-2657.

Feline et al. "Pseudomonic acid. Part 2. Biosynthesis of Pseudomonic Acid A." Journal Chemical Society, Perkin Trans. I. 1977, pp. 309-318.

Mantle et al. "Radiolabelling of the monate moiety in the study of pseudomonic acid biosynthesis." FEMS Microbiol. Lett. 1989, vol. 59, No. 12, pp. 55-58.

Martin et al. "Biosynthetic studies on pseudomonic acid (mupirocin), a novel antibiotic metabolite of Pseudomonas fluorescens." Journal Chemical Society, Perkin Trans. I. 1989, pp. 207-209.

Ward et al. "Mupirocin-A review of Its Antibacterial Activity, Pharmacokinetic Properties and Therapeutic Use," Drugs. 1986, vol. 32, No. 5, pp. 425-444.

Hughes et al. "Interaction of pseudomonic acid A with *Escherichia coli* B isoleucyl-tRNA synthetase." Biochemical Journal. 1980, vol. 191, pp. 209-219.

Chain et al. "Pseudomonic Acid. Part. 3. Structure of Pseudomonic Acid B" Journal Chemical Society, Perkin Trans. I. 1977, p. 318-322.

Chain et al. "Structure of Pseudomonic Acid, and Antibiotic from *Pseudomonas fluorescens*." Journal of the Chemical Society, Chemical Communications. Jan. 1974, No. 1, pp. 847-848.

Alexander et al. "The Chemistry of Pseudomonic Acid. Part 1. The Absolute Configuration of Pseudomonic Acid A." Journal of the Chemical Society, Perkin Transactions I, Organic and Bio-organic Chemistry. 1978, pp. 561-565.

Palleroni. "Pseudomonaceae." Bergey's Manual of Systematic Bacteriology. 1984, vol. 1, pp. 141-219.

* cited by examiner

PH CONTROLLED FERMENTATION PROCESS FOR PSEUDOMONIC ACID PRODUCTION

CROSS-REFERENCE TO RELATED APPLICATION

This application claims the benefit under 35 U.S.C. §119 (e) of the U.S. Provisional Patent Application Ser. No. 60/299,927 filed Jun. 21, 2001, the content of which is incorporated herein in its entirety.

FILED OF THE INVENTION

The present invention relates to a metabolically controlled fermentation process for preparing pseudomonic acid. More specifically, the present invention is directed to a fermentation process for preparing pseudomonic acid A by regulating the pH level of the fermentation culture medium via feeding with dextrose, a mineral salt such as calcium chloride, an acidic solution, or an alkali solution.

BACKGROUND OF THE INVENTION

Pseudomonic acid A, also known as mupirocin, represents a major component of pseudomonic acid. Pseudomonic acid A was first discovered by A. T. Fuller et al. in 1971 [Nature 234, 416 (1971)]. Pseudomonic acid A has the following chemical name and trade names: [2S-[2 alpha (E),3 beta, 4 beta, 5 alpha [2R*, 3R*(1R*, 2R*)]]]-9-[[3-Methyl-1-oxo-4-[tetrahydro-3,4-dihydroxy-5-[[3-(2-hydroxy-1-methylpropyl) oxiranyl]methyl]-2H-pyran-2-yl]-2-butenyl]oxy] nonanoic acid, pseudomonic acid A, trans-pseudomonic acid, BRL-4910A, Bactoderm, Bactroban, and Turixin. Pseudomonic acid has topical antibacterial therapeutic activity.

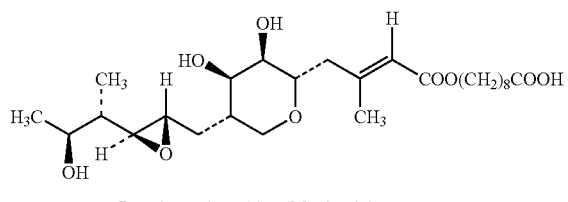

Pseudomonic Acid A (Mupirocin)

Pseudomonic acid A is a potent antibiotic against both Gram(+) bacteria (*Staphylococcus aureus, Streptococcus pyogenes, Streptococcus pneumoniae, Klebsiella pneumoniae*) and some Gram(−) bacteria (*Haemophilus influenzae, Neisseria gonorrhoeae*) [A. Ward, D. M. Campoli-Richards: Drugs 32, 425-444 (1986)]. The mode of action is believed to involve the inhibition of isoleucine-tRNA synthase enzyme that affects the peptide synthesis in bacteria [J. Hughes and G. Mellows: Biochem. Journal 191, 209-219 (1980)]. The disclosure of these references is incorporated by reference in its entirety.

Presently, pseudomonic acid is produced by cultivation of *Pseudomonas* sp. Conventional Fed Batch Technology involves feeding nutrients at the beginning of the fermentation process without regulating pH and nutrient concentration. Because of the fluctuation of pH levels and nutrient depletion during a Fed Batch fermentation process, the yield of pseudomonic acid is often diminished. A concomitant increase in impurity often represents a major drawback for Fed Batch Technology.

There is a constant need to improve fermentation processes for preparing pseudomonic acid, particularly increasing the degree of purity of pseudomonic acid A product (e.g., substantially reducing the pseudomonic acid B impurity).

SUMMARY OF THE INVENTION

According to one aspect, the present invention provides an improved process for producing pseudomonic acid, comprising the steps of:
  a) preparing a fermentation broth containing a pseudomonic acid producing micro-organism;
  b) regulating pH of the fermentation broth; and
  c) recovering the pseudomonic acid from the fermentation broth.

According to another aspect, the present invention provides an efficient process for producing pseudomonic acid that attains a high level of purity (i.e., the ratio of pseudomonic B impurity to pseudomonic acid A is less than 3%). Hence, the present invention provides an improved and economical fermentation process for preparing an increased yield of highly purified pseudomonic acid A.

According to another aspect, the present invention provides a fermentation process for pseudomonic acid production using the *Pseudonomas* sp. strain deposited under the code No. NCAIM (P)B 001235 in the National Collection of the Agricultural and Industrial Micro-organisms.

According to another aspect, the present invention provides a fermentation process whereby the pH of the fermentation culture medium is regulated to be at about 5.5-6.0 throughout the fermentation. Most preferably, the pH of the fermentation broth is regulated at about 5.7.

According to another aspect, the present invention provides a fermentation process for preparing pseudomonic acid, wherein the pH is regulated by feeding the fermentation culture medium with an assimilable carbon source. Preferably, the assimilable carbon source is dextrose.

According to another aspect, the present invention provides a fermentation process for preparing pseudomonic acid, wherein the dextrose is maintained at a level of less than about 0.5% in the fermentation broth during the production phase.

According to another aspect, the present invention provides a fermentation process for preparing pseudomonic acid, wherein the fermentation culture is fed with a solution containing at least 0.1% calcium chloride ($CaCl_2$) during the production phase of the fermentation.

According to another aspect, the present invention provides a fermentation process for preparing pseudomonic acid, wherein the pH of the fermentation culture medium is regulated by feeding the fermentation broth with an alkali solution and/or an acidic solution.

According to another aspect, the present invention provides a fermentation process for optimal combination of feeding of dextrose and an acidic solution. The present invention provides an optimal combination of feeding of dextrose and an acid that can stimulate the biosynthesis of pseudomonic acid during the fermentation and avoid a repression effect of the excess of the carbon source in the broth.

DETAILED DESCRIPTION OF THE INVENTION

Unless otherwise specified, the terms "%" refers to % weight vs. weight, "vvm" refers to volume of air/volume of fermentation broth/minute, "HPLC" refers to high pressure liquid chromatography. The term "dextrose" also refers to glucose.

As used herein, the terms "submerged culture" refers to a fermentation culture that is a liquid culture with stirring and aeration; "Fed Batch Technology" refers to a fermentation process, wherein one or more nutrient components (e.g., a carbon source or a salt) are fed only at the beginning of the fermentation process; "metabolically control" fermentation refers to a fermentation process during which the consumption of carbon or nitrogen source is regulated; "production phase" refers to a period of fermentation during which the required molecules are being biosynthesising; and "logarithmic phase" refers to a period of fermentation during which the micro-organism is multiplying in a logarithmically fashion.

As used herein, the term "a mineral salt" refers to a salt of biologically important element and trace element. Preferably, magnesium sulphate is used as a mineral salt that functions to regulate pH and some other additional effects. Most preferably, calcium chloride is used as a mineral salt.

As used herein, the term "assimilable" refers to a given micro-organism that has an enzyme system for absorption of nutrients and consumption or use or decompose of such nutrients to use in the biosynthesis of complex constituents of the micro-organism.

A preferred pseudomonic acid producing micro-organism for carrying out the fermentation process of the invention is *Pseudonomas* sp. strain. Alternative pseudomonic acid producing micro-organism include the *Pseudonomas* sp. progenies, its natural variants and mutants. Most preferably, the *Pseudonomas* sp. strain used is the code No. NCAIM (P)B 001235 deposited in the National Collection of the Agricultural and Industrial Micro-organisms.

Preferably, the pH of the fermentation broth is regulated such that pseudomonic acid A is increased and pseudomonic acid B is decreased (i.e., the ratio of pseudomonic B impurity to pseudomonic A is less than 3%). More preferably, the pH of the fermentation broth is regulated at a pH level between about 5.2-6.2. Most preferably, the pH of the fermentation broth is pH 5.7.

Preferably, *Pseudomonas* sp. strain is cultured in a submerged culture medium. Preferably, the fermentation culture is performed at a temperature within 20-30° C.

To regulate the pH of the fermentation culture, one preferred embodiment involves the feeding of an assimilable carbon source into the fermentation culture medium. A preferred embodiment of the assimilable carbon source is dextrose. Accordingly, dextrose feeding serves as a carbon source and its intermediate and end-products often reduces the pH of the fermentation broth. Most preferably, dextrose feeding is maintained at a level of less than about 0.5% dextrose in the fermentation broth during the production phase.

Other preferred embodiments for the assimilable carbon source include glycerol, vegetal and animal oils and fats.

When glycerol is used to feed a fermentation culture medium as a source of assimilable carbon, it does not have sufficient effect to reduce the pH of the fermentation broth. Accordingly, an acidic solution is often used to concomitantly feed the fermentation broth to achieve an optimal effect. Preferably, the acidic solutions include HCl, $HNO_3$ and $H_2SO4$. Most preferably, the acidic solution is HCl.

When the pH of the fermentation culture medium is low, an alkali solution is often used to feed the fermentation broth to reach an optimal pH level. Preferably, the alkali solution used to feed the fermentation broth include NaOH and KOH. Most preferably, the alkali solution is NaOH.

Another preferred embodiment to regulate the pH of the fermentation culture medium involves the feeding of a mineral salt. Preferably, a solution of calcium chloride is used to feed a fermentation culture medium. More preferably, a 0.1-0.8% (wt/wt) calcium chloride solution is used. Most preferably, a 0.1% (wt/wt) calcium chloride solution is used.

The process according to the invention is illustrated in details by the following but not limiting examples.

EXAMPLE 1

| | Seed medium, gm/liter | Main fermentation medium, gm/liter |
|---|---|---|
| Dextrose monohydrate | 20 | 20 |
| Soya bean meal | — | 50 |
| Glycerine | 5 | 10 |
| Corn step liquor | — | 5 |
| Sodium chloride | 0.5 | 5 |
| Potassium chloride | 0.5 | — |
| Calcium carbonate | 4 | 5 |
| Ammonium-sulphate | 2 | — |
| Potassium-dihydrogen-phosphate | 0.4 | — |
| Manganese chloride x $2H_2O$ | 0.03 | — |
| Magnesium sulphate | 0.4 | — |
| Sunflower oil | 2 | 10 |
| NaOH, HCl | pH setting | pH setting |
| pH before sterilisation | 7.0-7.2 | 6.5 ± 0.3 |

Culture of *Pseudomonas* sp. in Seed Medium

A seed medium (without dextrose) was prepared in a 60 liter vessel. The prepared seed medium (about 40-60 liters) was sterilised for about 45 min at a temperature of about 120° C.

A dextrose solution was prepared separately. The pH of the dextrose solution was adjusted using hydrochloric acid to about 4.0-5.0. The dextrose solution was sterilised for about 25 min. at a temperature of about 120° C. The sterilised dextrose solution was added into the seed medium to achieve a dextrose concentration of 20 gm/L.

The *Pseudomonas* sp. strain (i.e., NCAIM (P)B 001235) was inoculated into a sterilised seed medium (about 500 ml). The *Pseudomonas* sp. strain was allowed to grow in the seed medium until it reached to a logarithmic growth phase. The *Pseudomonas* cultivation was carried out with the following parameters:

Temperature: about 25±1° C.;
Head Pressure: about 0.4±0.1 bar;
Mixing Rate: about 400 rpm;
Aeration Ratio: about 0.5 vvm.

The total time for the seed stage was 24 hours.

Culture of *Pseudomonas* sp. in Fermentation Medium

A main fermentation medium was prepared in a 300 liter vessel. The prepared main fermentation medium (about 200 liters) was sterilised for about 45 min at a temperature of about 120° C.

A dextrose solution was prepared separately. The pH of the dextrose solution was adjusted using hydrochloric acid to about 4.0-5.0. The dextrose solution was sterilised for about 25 min. at about 120° C. The sterilised dextrose solution was added into the main fermentation medium.

After the main fermentation medium was prepared, the seed medium containing the *Pseudomonas* sp. strain after its seed stage was added. The ratio of the seed stage to the main fermentation medium was about 10% (wt/wt).

The cultivation of the fermentation broth was performed with the following parameters:

Temperature: about 25±1° C.;
Aeration Ratio: about 0.5-1.0 vvm;
Stirring Rate: about 300-600 rpm; and
Head Pressure: about 0.5 bar.

Both the stirring rate and the aeration rate were adjusted within the above-mentioned ranges in order to control the dissolved oxygen at a constant level of 30% throughout the entire fermentation process.

The duration of fermentation broth cultivation was about 64 hours. During the fermentation process, additional oil was fed into the fermentation broth if there was any foaming of the broth.

YIELD: The achieved yield of pseudomonic acid A was about 2,056 μg/gram fermentation broth as measured by HPLC. The pseudomonic acid B impurity was estimated to be about 18% (wt/wt) of the pseudomonic acid A.

Determination of Content and Purity of Pseudomonic A and Pseudomonic B:

Content and purity determination for pseudomonic A and pseudomonic B was based on the assay method of USP 24. The determination assay was performed with HPLC in which the respective concentrations of pseudomonic A and pseudomonic B was determined as well as the wt/wt ratio of pseudomonic A and pseudomonic B.

Chromatographic System Included:
Column: LiChrosper 100 RP-18, 5 m, 250-4;
Detector: UV 229 nm;
Flow rate: 0.7 ml/min;
Injection volume: 20 ul; and
Mobile phase: Prepare a suitable mixture of pH 6.3 phosphate buffer (0.05 M monobasic sodium phosphate) and acetonitrile (75:25).

Standard Solution:
Weighed Pseudomonic A and Pseudomonic B were added to a 100 ml volumetric flask followed by the addition of 25 ml of acetonitrile to form a mixture, the mixture was diluted with a phosphate buffer (pH 6.3) and then was mixed. The final concentration of standards were about 100 ug/ml.

Running time: about 15 minutes.

Sample Preparation from Fermentation Broth:
Transferred mupirocin fermentation broth (5 ml) to a 10.0 ml volumetric flask, and diluted with ethyl alcohol (96%);
Ultrasonicated for 20 minutes;
Centrifuged for 15 minutes at 5,000 rpm;
Diluted the supernatant (1.0 ml) to 10.0 ml with the mobile phase;
Filtered through a Millipore filter (0.45 micron).

EXAMPLE 2

|  | Seed medium, gram/liter | Main fermentation medium, gram/liter |
| --- | --- | --- |
| Dextrose monohydrate | 20 | 20 |
| Soya bean meal | — | 50 |
| Glycerine | 5 | 10 |
| Corn step liquor | — | 5 |
| Sodium chloride | 0.5 | 5 |
| Potassium chloride | 0.5 | — |
| Calcium chloride | — | 3 |
| Calcium carbonate | 4 | 4 |
| Ammonium-sulphate | 2 | — |
| Potassium-dihydrogen-phosphate | 0.4 | — |
| Manganese chloride x 2H$_2$O | 0.03 | — |
| Magnesium sulphate | 0.4 | — |
| Sunflower oil | 2 | 10 |
| NaOH, HCl | pH setting | pH setting |
| pH before sterilisation | 7.0-7.2 | 6.5 ± 0.3 |

Culture of *Pseudomonas* sp. in Seed Medium

A seed medium (without dextrose) was prepared in a 60 liter vessel. The prepared seed medium (about 40-60 liters) was sterilised for about 45 min. at a temperature of about 120° C.

A dextrose solution was prepared separately. The pH of the dextrose solution was adjusted using hydrochloric acid to about 4.0-5.0. The dextrose solution was sterilised for about 25 min. at about 120° C. The sterilised dextrose solution was added into the seed medium at a dextrose concentration of 20 gm/L.

The *Pseudomonas* sp. strain (i.e., NCAIM (P)B 001235) was inoculated into a sterilised seed medium (500 ml). The *Pseudomonas* sp. strain was allowed to grow in the seed medium until it reached to a logarithmic growth phase. The *Pseudomonas* cultivation was carried out with the following parameters:

Temperature: about 25±1° C.;
Head Pressure: about 0.4±0,1 bar;
Mixing Rate: about 400 rpm; and
Aeration Ratio: about 0.5 vvm.

The total time for the seed stage was 24 hours.

Culture of *Pseudomonas* sp. in Fermentation Medium

A main fermentation medium was prepared to a 300 liter vessel. The prepared main fermentation medium (about 200 liters) was sterilised for about 45 min. at a temperature of about 120° C.

A dextrose solution was prepared separately. The pH of the dextrose solution was adjusted using hydrochloric acid to about 4.0-5.0. The dextrose solution was sterilised for about 25 min. at about 120° C. The sterilised dextrose solution was added into the main fermentation medium to achieve a concentration of 20 gm/L.

After the main fermentation medium was prepared, the seed medium containing the *Pseudomonas* sp. strain after its seed stage was added. The ratio of the seed stage to the main fermentation medium was about 10% (wt/wt).

The *Pseudomonas* sp. cultivation in the fermentation broth was performed with the following parameters:

Temperature: about 25±1° C.;
Aeration Rate: about 0.5-1.0 vvm;
Stirring Rate: about 300-600 rpm, and
Head Pressure: about 0.5 bar.

Both the stirring rate and the aeration rate were adjusted within the above-mentioned ranges in order to control the dissolved oxygen at a constant level of 30% throughout the fermentation process.

When the fermentation broth reached to a pH of about 5.5-5.8, the pH began to increase. Throughout the fermentation broth, the pH was regulated at a constant level of about 5.5-6.0. This was achieved by feeding hydrochloric acid solution into the fermentation broth. The feeding rate of hydrochloric acid varied depending on the actual pH of the broth.

The duration of fermentation broth cultivation was about 66 hours. During the fermentation broth, additional oil was fed into the fermentation broth if there was any foaming of the broth.

YIELD: The achieved yield of pseudomonic acid was about 2,251 μg/gram fermentation broth as measured by HPLC. The pseudomonic acid B impurity was estimated to be about 1.6% (wt/wt) of the pseudomonic acid A.

EXAMPLE 3

In this example, the preparation of seed medium, main fermentation medium and the culturing *Pseudomonas* sp. strain in the seed medium and the main fermentation medium were carried out in accordance with Example 2.

The cultivation of the fermentation broth was also performed with the same culture parameters as defined in Example 2.

However, the pH of the fermentation broth in this example was regulated using a different method. Instead of feeding the fermentation broth with hydrochloric acid, the pH was regulated with feeding with a dextrose solution.

It was observed that when the fermentation broth reached to a pH of about 5.5-5.8, the pH began to increase. In this example, the pH was regulated at a constant level of about 5.5-6.0. This was achieved by feeding with a dextrose solution. The feeding rate of the dextrose solution into the fermentation broth depended on the actual pH and the actual dextrose content in the broth. During the dextrose feeding, the glucose level was not allowed to be higher than about 0.5% (wt/wt). When the pH raised above 5.8-6.0 and the dextrose level was higher than 0.45% (wt/wt), the pH is regulated by feeding the fermentation broth with hydrochloric acid instead of dextrose.

The duration of fermentation broth cultivation was about 65 hours. During the fermentation process, additional oil was fed if there was any foaming YIELD: The achieved yield of pseudomonic acid A was about 3,021 µg/gram fermentation broth as measured by HPLC. The pseudomonic acid B impurity was estimated to be about 2.9% (wt/wt) of the pseudomonic acid A.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosure of which is incorporated by reference in their entireties.

What is claimed is:

1. A fermentation process for producing pseudomonic acid, comprising the steps of:
   a. preparing a fermentation broth containing the pseudomonic acid producing *Pseudomonas* strain NCAIM (P)B 001235, wherein the organism produces pseudomonic acid B as an impurity, said impurity production depending on pH regulation of the fermentation broth;
   b. regulating pH of the fermentation broth by maintaining the pH within about 5.2 to 6.2 during the production phase of fermentation; and
   c. recovering the pseudomonic acid from the fermentation broth.

2. The fermentation process of claim 1, wherein the fermentation is a submerged culture.

3. The fermentation process of claim 1, wherein the fermentation is maintained at a temperature of about 20° C.-30° C.

4. The fermentation process of claim 1, wherein the pH of the fermentation broth is regulated between about 5.5-6.0.

5. The fermentation process of claim 1, wherein the pH of the fermentation broth is regulated at about 5.7.

6. The fermentation process of claim 1, wherein the pH of the fermentation broth is regulated by supplying the fermentation broth with an assimilable carbon source.

7. The fermentation process of claim 6, wherein the assimilable carbon source is dextrose.

8. The process of claim 7, wherein the dextrose level in the fermentation broth is maintained at a level less than about 0.5% (wt/wt).

9. The fermentation process of claim 1, wherein the pH of the fermentation broth is regulated by concomitant supplying of the fermentation broth with an assimilable carbon source and an acidic solution.

10. The fermentation process of claim 9, wherein the assimilable carbon source is glycerol and the acidic solution is hydrochloric acid solution.

11. The fermentation process of claim 1, wherein the pH of the fermentation broth is regulated by supplying the fermentation broth with a mineral salt.

12. The fermentation process of claim 11, wherein the mineral salt is a calcium chloride solution.

13. The fermentation process of claim 12, wherein the calcium chloride solution is about 0.1%-0.8% (wt/wt).

14. The fermentation process of claim 12, wherein the calcium chloride solution is about 0.3% (wt/wt).

15. The fermentation process of claim 1, wherein the pH of the fermentation broth is regulated by supplying the fermentation broth with an alkali solution.

16. The fennentation process of claim 15, wherein the alkali solution is selected from the group consisting of sodium hydroxide and potassium hydroxide.

17. The fermentation process of claim 15, wherein the alkali solution is potassium hydroxide.

18. The fermentation process of claim 1, wherein the pH of the fermentation broth is regulated by supplying the fermentation broth with an acidic solution.

19. The fermentation process of claim 18, wherein the acidic solution is selected from the group consisting of nitric acid ($HNO_3$) solution, sulphuric acid ($H_2SO_4$) solution and hydrochloric acid (HCl) solution.

20. The fermentation process of claim 18, wherein the acidic solution is hydrochloric acid solution.

21. The process of claim 1, wherein the process results in a pseudomonic acid of having 18% or less (wt/wt) of pseudomonic acid B in respect to pseudomonic acid A.

22. The process of claim 21, wherein the pseudomonic acid has less than 3% (wt/wt) of pseudomonic acid B.

23. A fermentation process for producing pseudomonic acid, comprising the steps of:
   a. preparing a fermentation broth including the pseudomonic acid producing *Pseudomonas* strain NCAIM (P)B 001235 and calcium chloride, wherein the organism produces pseudomonic acid B as an impurity, said impurity production depending on pH regulation of the fermentation broth;
   b. regulating pH of the fermentation broth by maintaining a pH within a range of about 5.2-6.2 during the production phase of fermentation through supplying dextrose, and an acid if necessary to keep the pH within the range; and
   c. recovering the pseudomonic acid from the fermentation broth.

24. The fermentation process of claim 23, wherein the regulating pH involves maintaining a pH of about 5.5-6.

25. The fermentation process of claim 24, wherein the regulating pH involves a maximum dextrose level of about 0.5% (wt/wt).

26. The fermentation process of claim 24, wherein an acid is added when the pH is at least 5.8 and the dextrose level is at least 0.45% (wt/wt).

27. The fermentation process of claim 23, wherein the process results in a pseudomonic acid of having 18% or less (wt/wt) of pseudomonic acid B in respect to pseudomonic acid A.

28. The fermentation process of claim 27, wherein the pseudomonic acid has less than 3% (wt/wt) of pseudomonic acid B.

* * * * *

UNITED STATES PATENT AND TRADEMARK OFFICE
CERTIFICATE OF CORRECTION

PATENT NO. : 7,439,045 B2
APPLICATION NO. : 10/177026
DATED : October 21, 2008
INVENTOR(S) : Gulyas et al.

Page 1 of 1

It is certified that error appears in the above-identified patent and that said Letters Patent is hereby corrected as shown below:

Column 8
Line 16, change "fennentation" to --fermentation--
Line 31, change "acid of having" to --acid having--
Line 32, change "in respect" to --with respect--
Line 59, change "acid of having" to --acid having--
Line 60, change "in respect" to --with respect--

Signed and Sealed this

Twenty-fifth Day of August, 2009

David J. Kappos
*Director of the United States Patent and Trademark Office*